United States Patent
Chen

(10) Patent No.: US 9,470,648 B2
(45) Date of Patent: Oct. 18, 2016

(54) ELECTRODE STRIP AND SENSOR STRIP AND SYSTEM THEREOF

(71) Applicant: APEX BIOTECHNOLOGY CORP., Hsinchu (TW)

(72) Inventor: Sz Hau Chen, Taipei (TW)

(73) Assignee: APEX BIOTECHNOLOGY CORP., Hsinchu (TW)

( * ) Notice: Subject to any disclaimer, the term of this patent is extended or adjusted under 35 U.S.C. 154(b) by 497 days.

(21) Appl. No.: 14/136,989

(22) Filed: Dec. 20, 2013

(65) Prior Publication Data
US 2014/0238854 A1    Aug. 28, 2014

(30) Foreign Application Priority Data
Feb. 25, 2013   (TW) .............................. 102106485 A

(51) Int. Cl.
*G01N 27/327*    (2006.01)

(52) U.S. Cl.
CPC ...... *G01N 27/3272* (2013.01); *G01N 27/3274* (2013.01)

(58) Field of Classification Search
CPC ..................... G01N 27/3272; G01N 27/3274; G01N 27/3275
See application file for complete search history.

(56) References Cited

U.S. PATENT DOCUMENTS

| 6,258,230 | B1  | 7/2001 | Shen et al. |
| 2006/0042941 | A1* | 3/2006 | Kusaka ............ B01L 3/502715 204/403.01 |
| 2007/0023283 | A1* | 2/2007 | Huang ............. B29C 45/14639 204/400 |

FOREIGN PATENT DOCUMENTS

| CN | 1839313 A | 9/2006 |
| CN | 101271106 | 9/2008 |
| CN | 102128932 | 7/2011 |
| CN | 102128932 A | 7/2011 |
| JP | 2004279150 | 10/2004 |
| JP | 2007521498 | 8/2007 |
| TW | 200819745 A | 5/2008 |
| TW | 201120439 A | 6/2011 |

OTHER PUBLICATIONS

Office Action issued on Aug. 6, 2013 by TIPO for the counterpart TW Patent Application No. 102106485 cites CN 101271106, JP 2007521498, JP 2004279150, and CN 102128932.
English Abstract of Office Action issued on Aug. 6, 2013 by TIPO for the counterpart TW Patent Application No. 102106485.
(Continued)

*Primary Examiner* — Susan D Leong
(74) *Attorney, Agent, or Firm* — WPAT, P.C., Intellectual Property Attorneys; Anthony King

(57) ABSTRACT

The present disclosure relates to an electrode strip, a sensor strip and a system thereof. The electrode strip includes a substrate, an electrode layer, an insulation layer and a cover. The electrode layer is disposed on the substrate. The electrode layer includes a first electrode set and a second electrode set. The insulation layer includes a groove, a first protrusion and a second protrusion. The first protrusion and the second protrusion divide the groove into two reactive areas such as a first reactive area and a second reactive area. The cover includes a vent-hole connecting to the groove, and the cover is disposed on the insulation layer.

15 Claims, 16 Drawing Sheets

(56) References Cited

OTHER PUBLICATIONS

English Abstracts of CN 101271106, JP 2007521498, JP 2004279150, and CN 102128932.
Office action and Search Report dated Dec. 1, 2015 from the China counterpart application 2013100712552.
English abstract translation of the office action dated Dec. 1, 2015 from the China counterpart application 2013100712552.
English abstract translation of TW201120439A.
English abstract translation of TW200819745A.
English abstract translation of CN102128932A.
English abstract translation of CN1839313A.

* cited by examiner

ELECTRODE STRIP AND SENSOR STRIP AND SYSTEM THEREOF

The present application claims priority from Taiwanese application Ser. No. 102106485, filed on Feb. 25, 2013, of the same title and inventorship herewith.

BACKGROUND

1. Technical Field

The present disclosure relates to an electrode strip, a sensor strip and a system thereof, and more particularly, to an electrode strip and a sensor strip having two reactive areas. Notably, there is a time difference between an entrance of the sample liquids into a first reactive area and an entrance of the sample liquids into a second reactive area.

2. Background

Electrodes made by utilizing electrochemical methods can be divided into two types: enzymatic electrodes and non-enzymatic electrodes. At the present time, the majority of electrodes mentioned in technical literature and used in biological substance measuring are enzymatic electrodes, such as well-commercialized blood sugar electrodes. In regard to non-enzymatic electrodes, most of them are used in the testing of general chemical compounds, such as pH electrodes for testing hydrogen ions. Since many enzymatic electrodes have restrictive conditions for moisture preservation, complicated manufacturing processes, and overelaborate control conditions, manufacturing costs are quite high and mass production is not feasible, and thus, they are only suitable for use by technicians in research organizations and large scale medical testing units.

Relating to the prior art of non-enzymatic electrode strips, such as an electric current non-enzymatic electrode strip disclosed in U.S. Pat. No. 6,258,230 B1, the manufacturing process uses screen printing to spread the reaction layer formulation to cover two electrode systems. The composition of the reaction layer formulation requires large amounts of polymers mixed with a salt buffer. However, an analyte concentration, measured by the above-identified non-enzymatic electrode strips, is usually disrupted by variant hematocrit factors in the blood samples.

The electrochemical method is one of the typical methods for measuring analyte concentrations and involves amperometric responses indicative of the concentration of the analyte. An important limitation of electrochemical methods of measuring the concentration of the analyte in blood is the effect of confounding variables on the diffusion of analyte and the various active ingredients of the reagent. Moreover, the electrochemical method has a problem in that the accuracy of the analyte concentration is disrupted by hematocrit concentrations (a ratio of the volume of packed red blood cells to the total blood volume).

The normal hematocrit range for an average human being is about 35% to about 45%, though in extreme cases, the hematocrit may range from about 20% to about 70%. The mean hematocrit range for a neonatal infant is about 53% to about 69%.

Variations in a volume of red blood cells within blood can cause variations in glucose readings measured by electrochemical sensor strips. Typically, a negative bias (i.e., lower calculated analyte concentration) is observed at high hematocrit levels, while a positive bias (i.e., higher calculated analyte concentration) is observed at low hematocrit levels. At high hematocrit levels, the red blood cells may impede the reaction of enzymes and electrochemical mediators; reduce the rate of chemistry dissolution since there is less plasma volume to solvate the chemical reactants; and slow diffusion of the mediator, causing a lower measured current result. Conversely, low hematocrit is levels can cause a higher measured current result. In addition, the blood sample resistance is also hematocrit dependent, which can affect voltage and/or current measurements.

Additionally, the variation of hematocrit levels is extremely broad, and therefore, needs to be measured by a biosensor and biosensor strips. It is highly crucial to design biosensor strips and a biosensor which effectively prevent hematocrit interference. How to make a system and method to prevent hematocrit interference of an analyte measurement is needed by the present related manufactory.

SUMMARY

In order to improve the above-identified disadvantage, the present disclosure provides a sensor strip and an electrode strip for hematocrit correction. The sensor strip and the electrode strip have two electrode sets in different reactive areas for measuring either a hematocrit concentration or the analyte concentration.

In accordance with the above-mentioned disadvantage, the present disclosure provides a sensor strip and an electrode strip having two protrusions which are configured to form two separated reactive areas. Since the two protrusions are enabled to avoid reflux of the sample liquids from another reactive area, the sensor strip and the electrode strip avoid cross-talking between direct current (DC) signals and alternating current (AC) signals in the same reactive area or same electrode set. Because the present disclosure does not require an appropriate temperature for correcting the analyte concentration, an electrode strip or a sensor strip includes a strengthened structure and provides simple operations and low cost requirements.

The present disclosure further provides an electrode strip having two reactive areas. The electrode strip includes a substrate, an electrode layer, an insulation layer, and a cover.

The electrode layer is disposed on the substrate and includes a first electrode set and a second electrode set.

The electrode layer further includes a third electrode set, which is disposed at the second reactive area. The third electrode set is disposed adjacent to an end of a groove. The third electrode set is configured to detect whether the sample liquids flow over the surface of the groove.

The insulation layer includes the groove, a first protrusion and a second protrusion.

The groove includes a first long side and a second long side. The first protrusion is configured to extend from the first long side toward the groove, while the second protrusion is configured to extend from the second long side toward the groove. The first protrusion and the second protrusion divide the groove into a first reactive area and a second reactive area.

In addition, a surface area of the first reactive area is larger than a surface area of the second reactive area.

The first protrusion and the second protrusion form a gap. A is first length includes a length of a short side of the first protrusion, a length of the gap, and a length of a short side of the second protrusion. A ratio of a first length to a length of either the first long side or second long side is from about 5% to about 30%. Additionally, a ratio of a length of either the long side of the first protrusion or the long side of the second protrusion to a length of a short side of the groove is from about 60% to about 90%.

The first electrode set is disposed in the first reactive area, while the second electrode set is disposed in the second reactive area. Thus, the first electrode does not cross-talk with the second electrode set.

The cover includes a vent-hole connecting with the groove, and the cover is disposed on the insulation layer.

The vent-hole connects with the second reactive area and is configured to form a capillary attraction which drives the sample liquid into the second reactive area from the first reactive area.

A bottom of the first protrusion connects with a surface of the electrode layer while a top portion of the first protrusion connects with the cover.

The first protrusion and the second protrusion are configured to alter the direction of the sample liquids flowing into the groove so as to avoid reflux.

The first protrusion and the second protrusion are configured to extend from opposing sides so as to form a gap between the first is protrusion and the second protrusion. A flowing length includes the length of the long side of the first protrusion, the length of the short side of the first protrusion, a length of the gap, the length of the short side of the second protrusion and the length of the long side of the second protrusion.

The flowing length is configured to postpone the sample liquids reaching the second reactive area from the first reactive area so as to generate a delay time.

The present disclosure further provides a sensor strip having two reactive areas. The sensor strip includes a substrate, an electrode layer and a reactive layer.

The electrode layer is disposed on the substrate and includes a first electrode set and a second electrode set.

The electrode layer further includes a third electrode set, which is disposed in the second reactive area. The third electrode set is disposed adjacent to an end of an opening and configured to detect whether the sample liquids flow over the surface of the opening.

The reactive layer includes the opening, a first protrusion, a second protrusion and a vent-hole.

The first protrusion is disposed at a wall of the opening and extends toward the opening while the second protrusion is disposed at the wall of the opening and extends toward the opening. The first protrusion and the second protrusion divide the opening into a first reactive area and a second reactive area.

The first protrusion is configured to narrow a bore of the opening to form a first inner bore, while the second protrusion is configured to narrow a bore of the opening to form a second inner bore. The first inner bore is located opposite to the second inner bore.

The vent-hole connects with the opening. The first electrode set is disposed in the first reactive area while the second electrode set is disposed in the second reactive area.

The first electrode set is configured to measure a hematocrit concentration.

The second electrode set is configured to measure an analyte concentration and receive an electric signal, which includes an alternating current (AC) signal or a direct current (DC) signal.

The present disclosure further provides a measurement system with hematocrit correction that includes the above-mentioned electrode strip or sensor strip, and a sensor.

The sensor, configured to electrically connect with either the electrode strip or the sensor strip, includes a power source, a detector and a microprocessor.

The power source is configured to transmit a direct current signal or an alternating current signal to the first electrode set so as to measure a hematocrit concentration.

The detector is configured to detect a first reactive value in response to the hematocrit concentration and a second reactive value in is response to the analyte concentration. The microprocessor is configured to calculate the hematocrit-corrected analyte concentration in response to the first reactive value and the second reactive value.

Another function of the present disclosure will be described in the following paragraphs. Certain functions can be realized in the present section, while the other functions can be realized in the detailed description. In addition, the indicated components and the assembly can be explained and achieved by the details of the present disclosure. Notably, the previous explanation and the following description are demonstrated and are not limited to the scope of the present disclosure.

The foregoing has outlined rather broadly the features and technical benefits of the disclosure in order that the detailed description of the disclosure that follows may be better understood. Additional features and benefits of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the disclosure. It should also be realized by those skilled in the art that such equivalent constructions do not depart from the spirit and scope of the disclosure as set forth in the appended claims.

BRIEF DESCRIPTION OF THE DRAWINGS

The accompanying drawings, which are incorporated in and is constitute a part of this specification, illustrate embodiments of the disclosure and, together with the description, serve to explain the principles of the invention.

The foregoing summary, as well as the following detailed description of the invention, will be better understood when read in conjunction with the appended drawings. For the purpose of illustrating the invention, there are shown in the drawings examples which are presently preferred. It should be understood, however, that the invention is not limited to the precise arrangements and instrumentalities shown.

Figure 1:
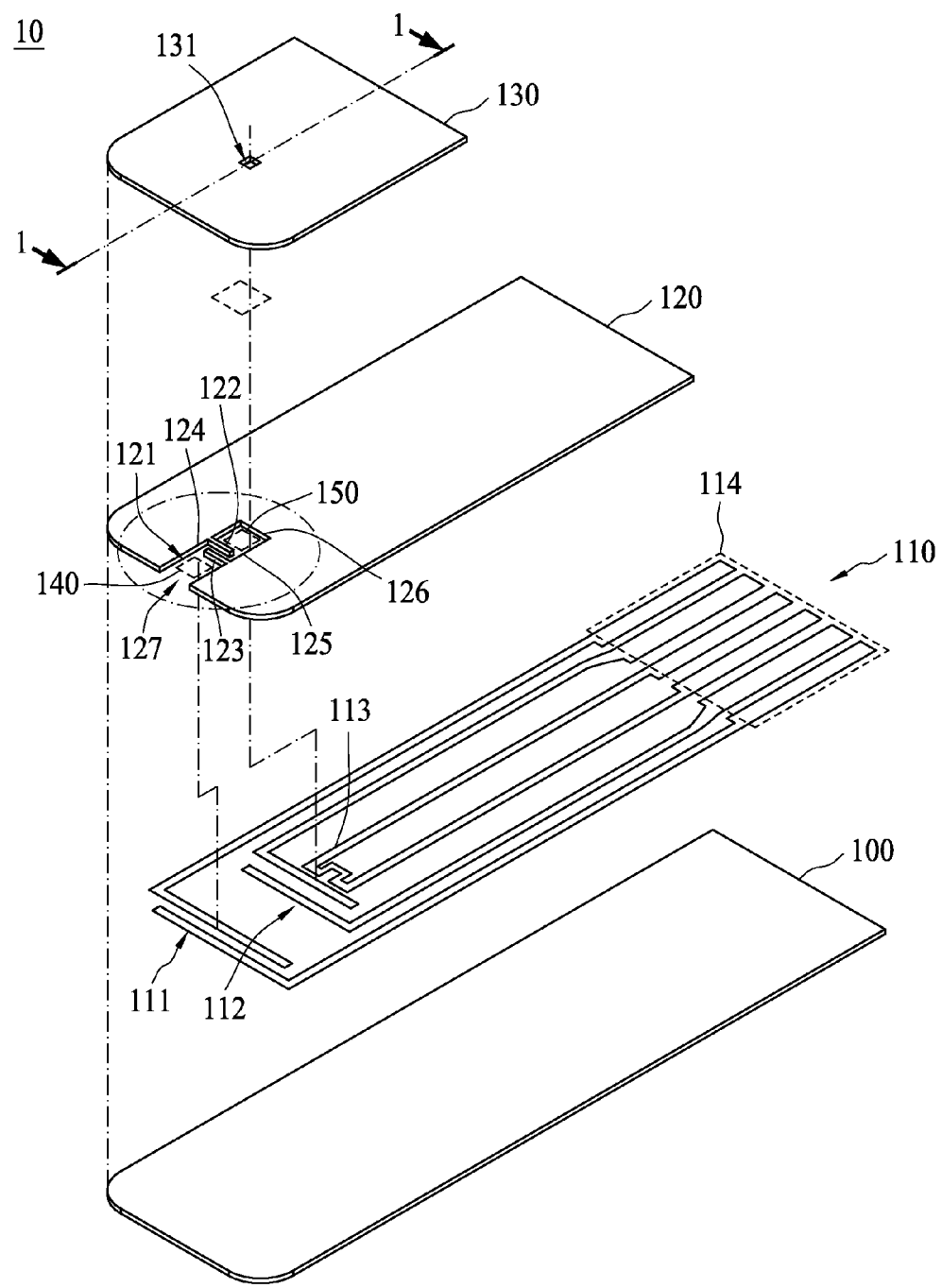
Figure 2:
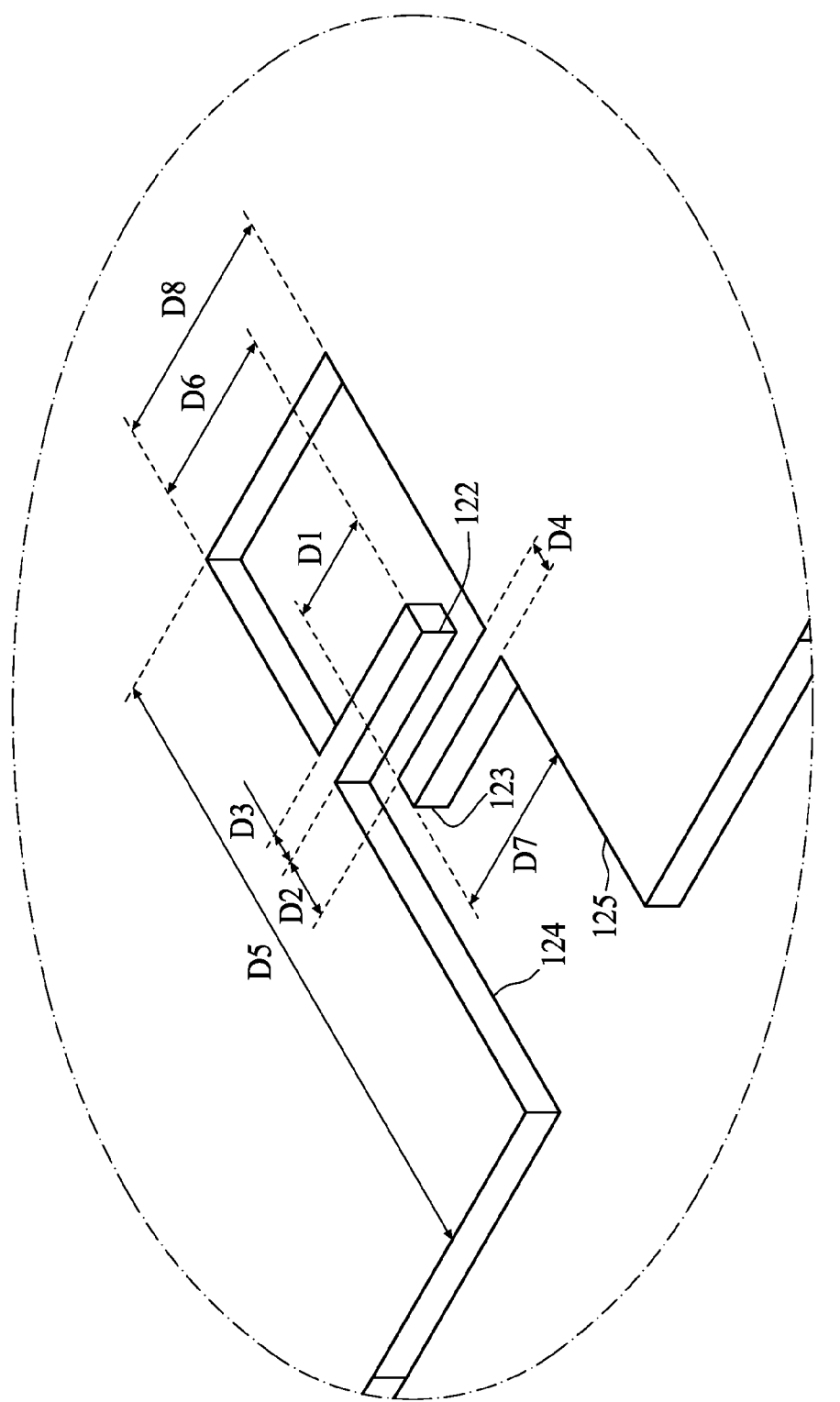
Figure 3:
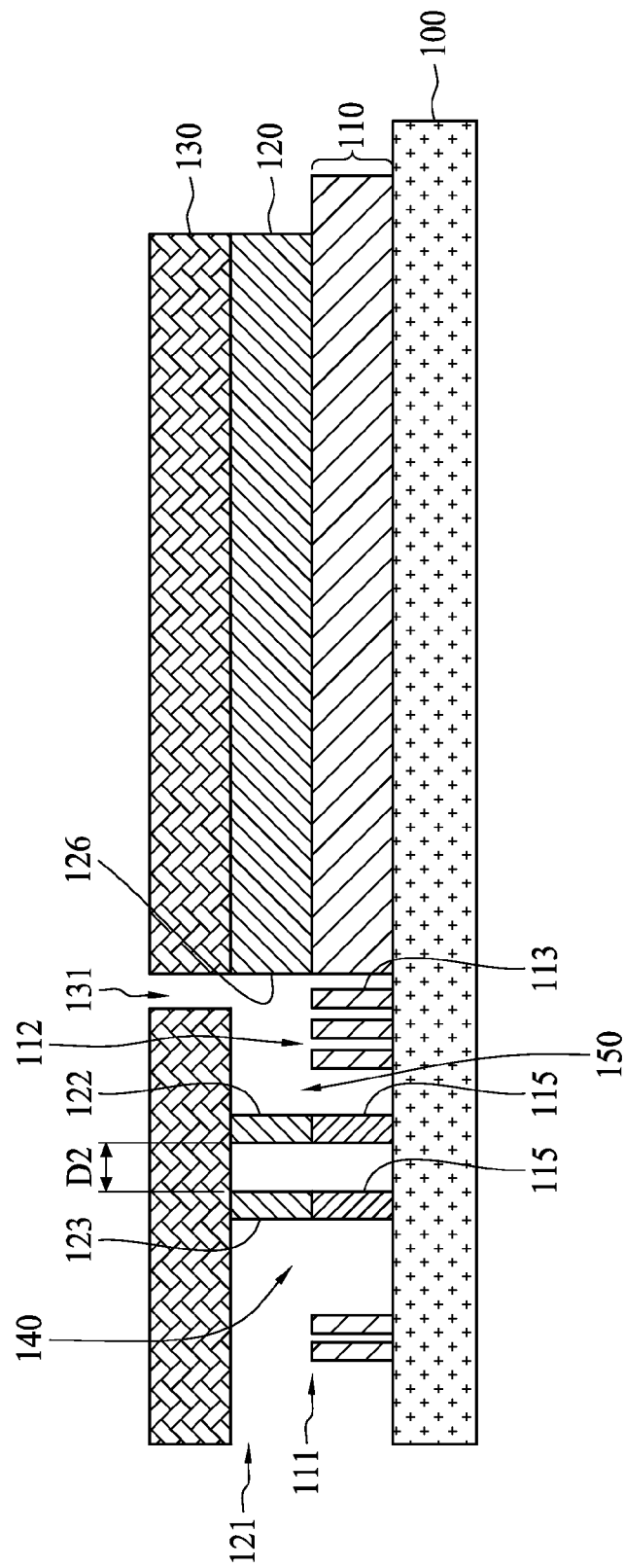
Figure 4:
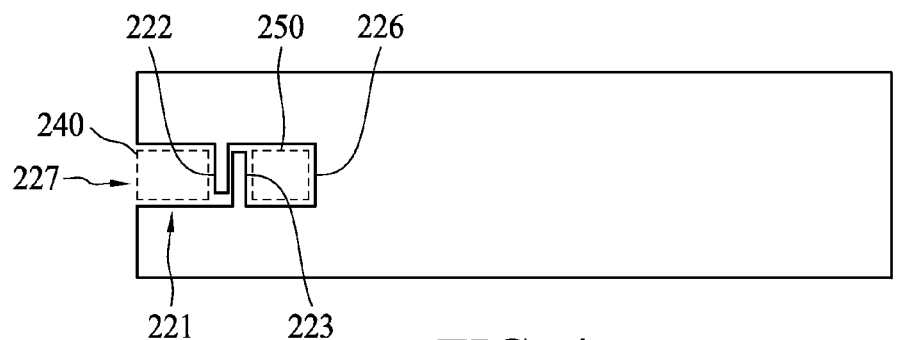
Figure 5:
Figure 6:
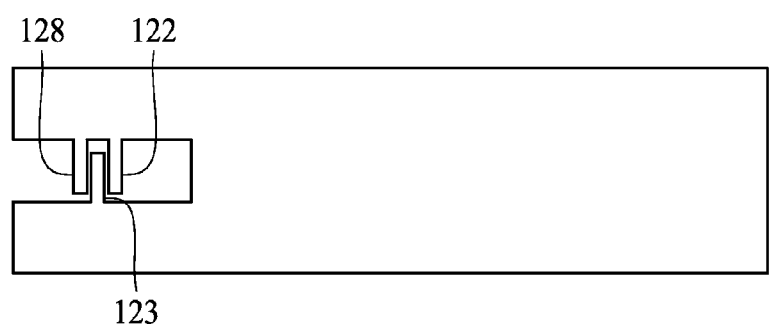
Figure 7:
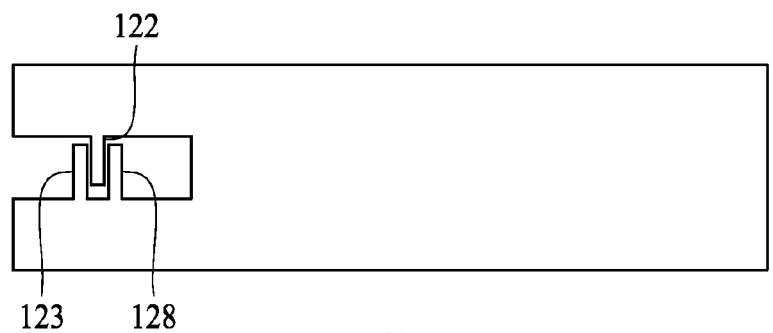
Figure 8:
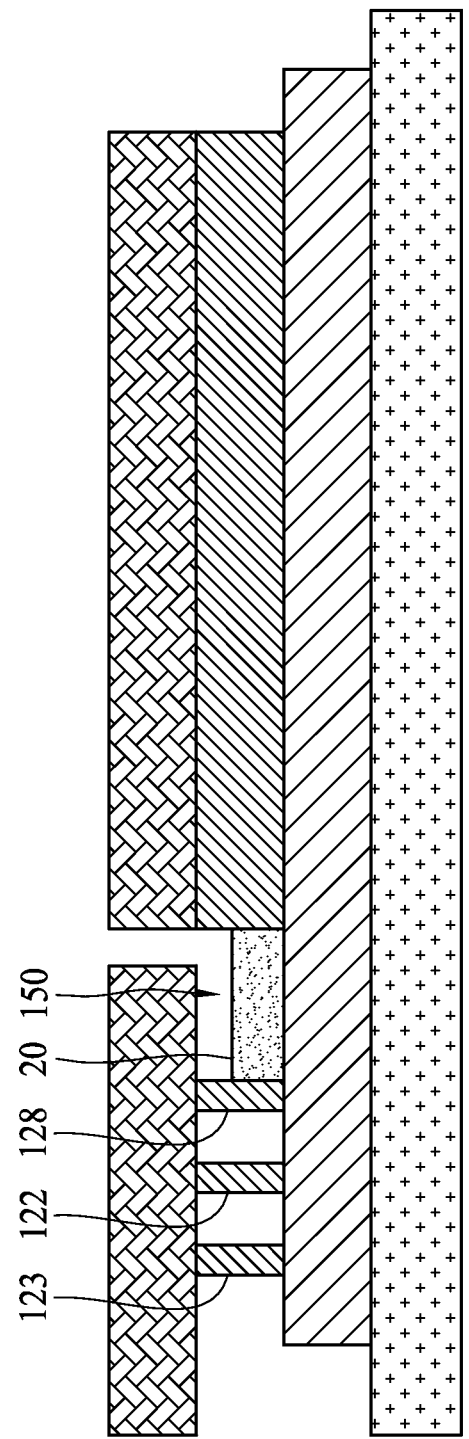
Figure 9:
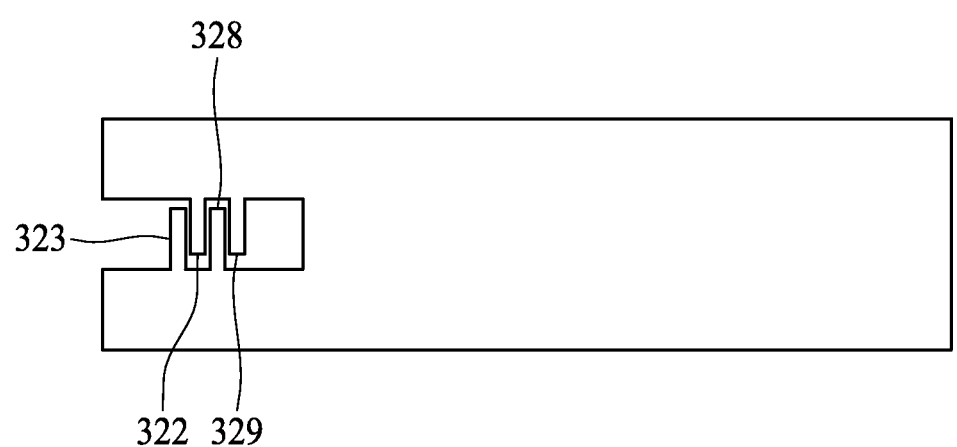
Figure 10:
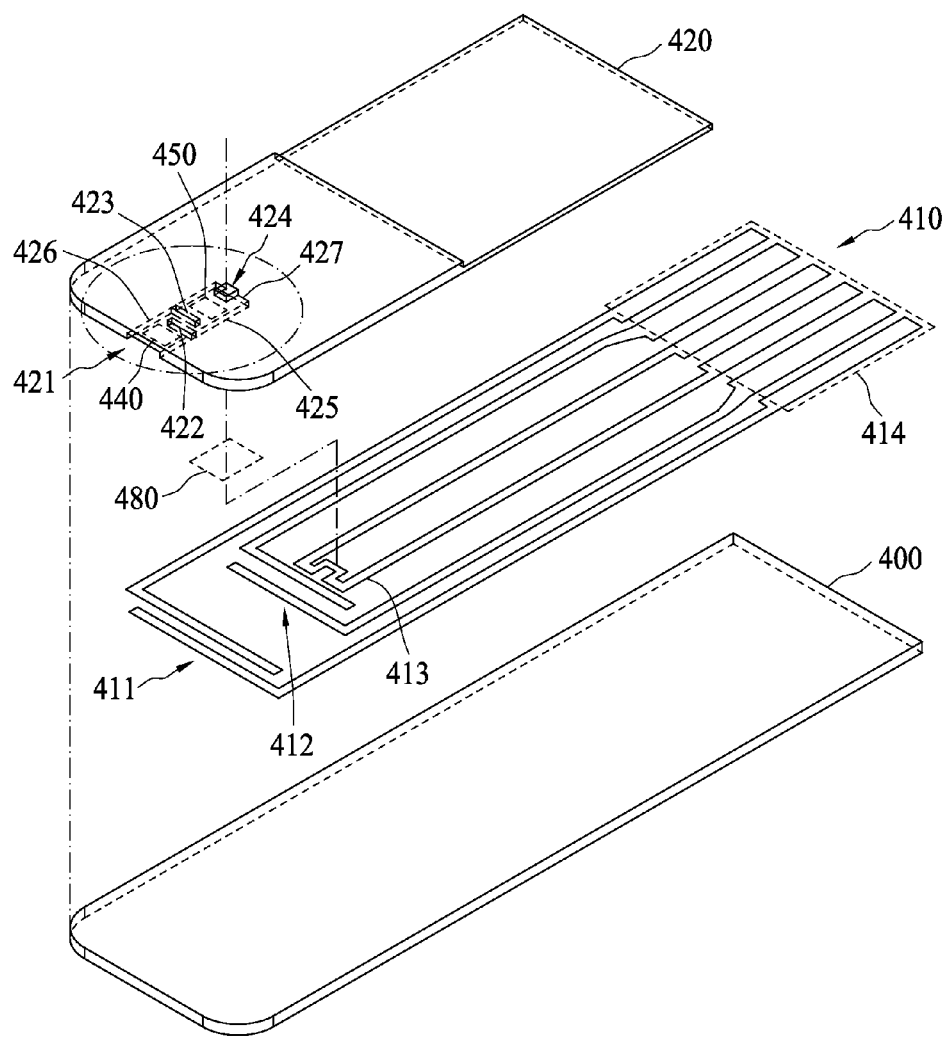
Figure 11:
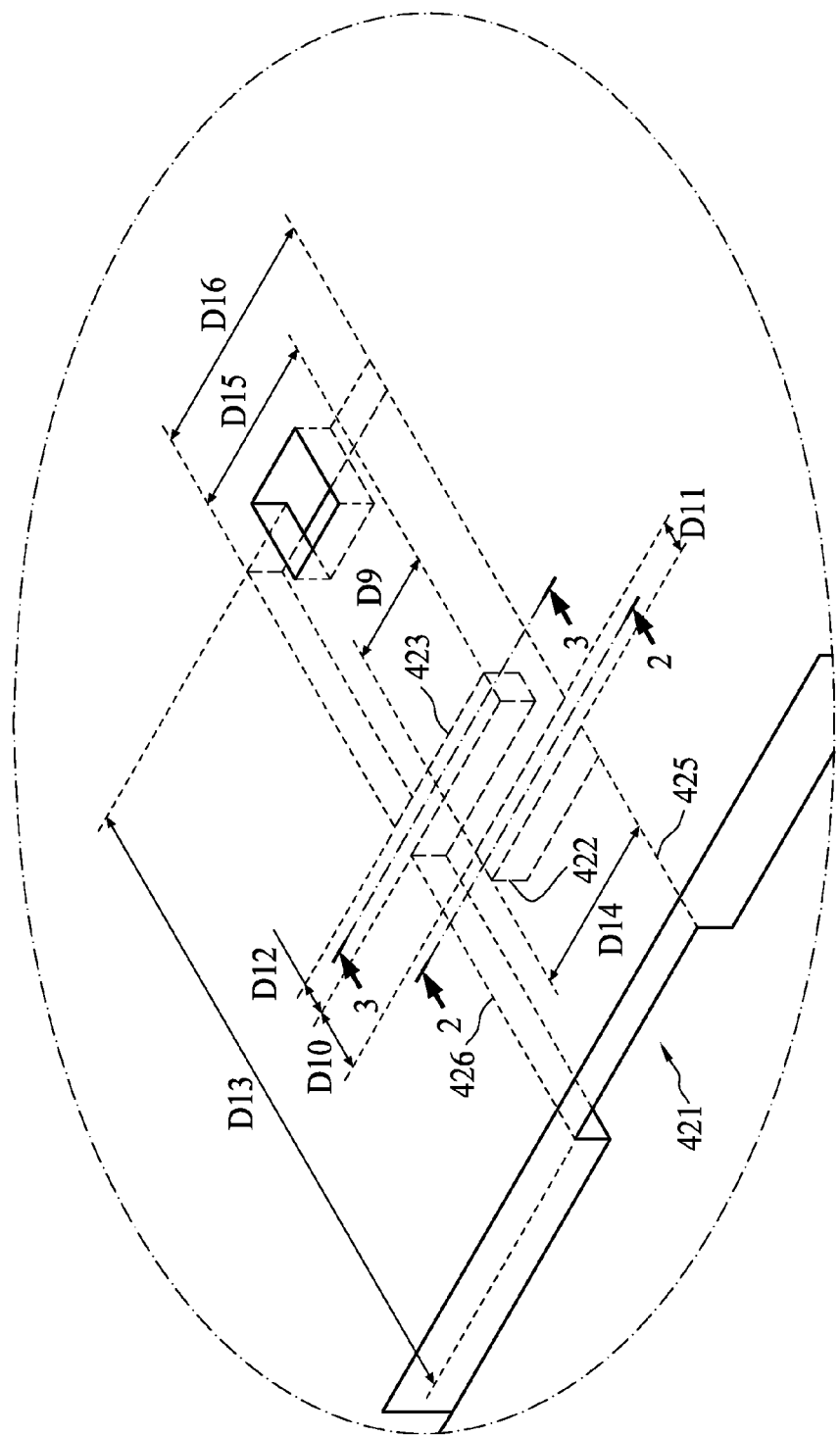
Figure 12:
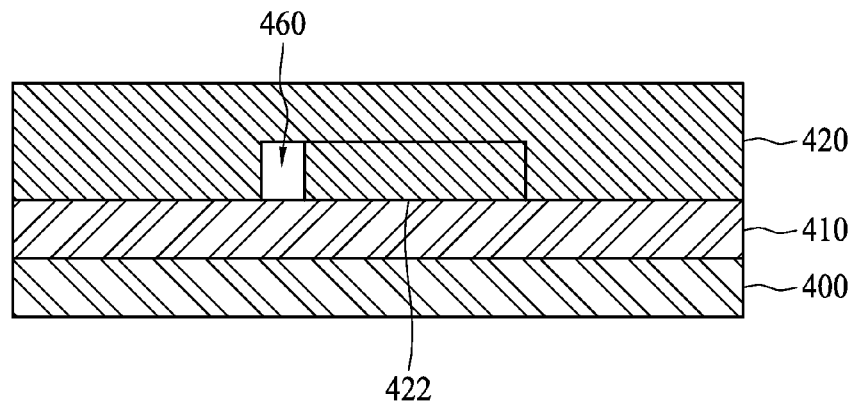
Figure 13:
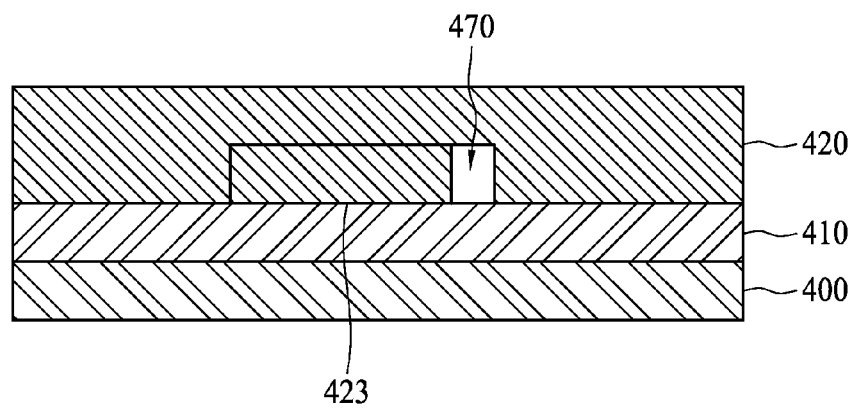
Figure 14:
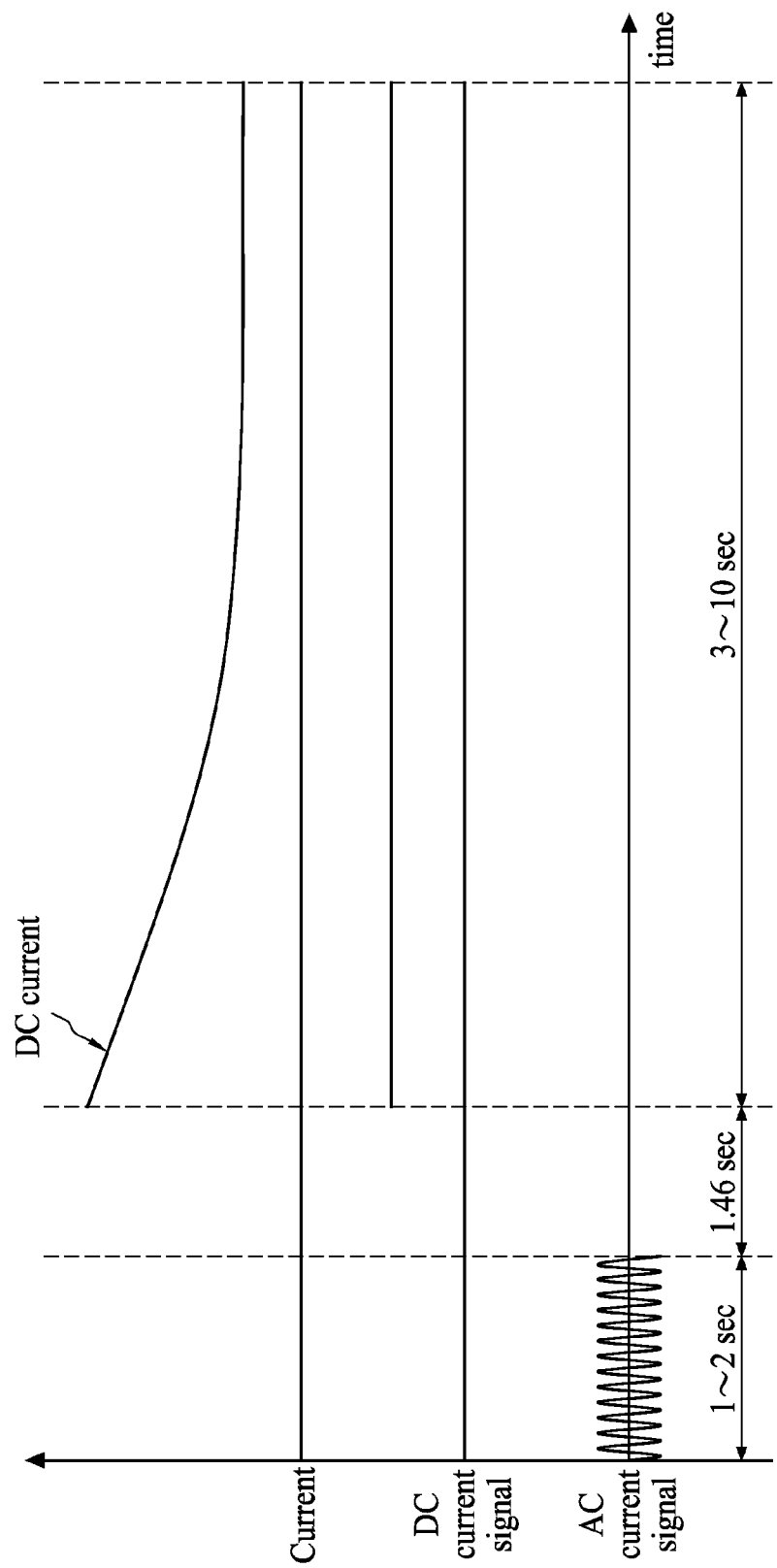
Figure 15:
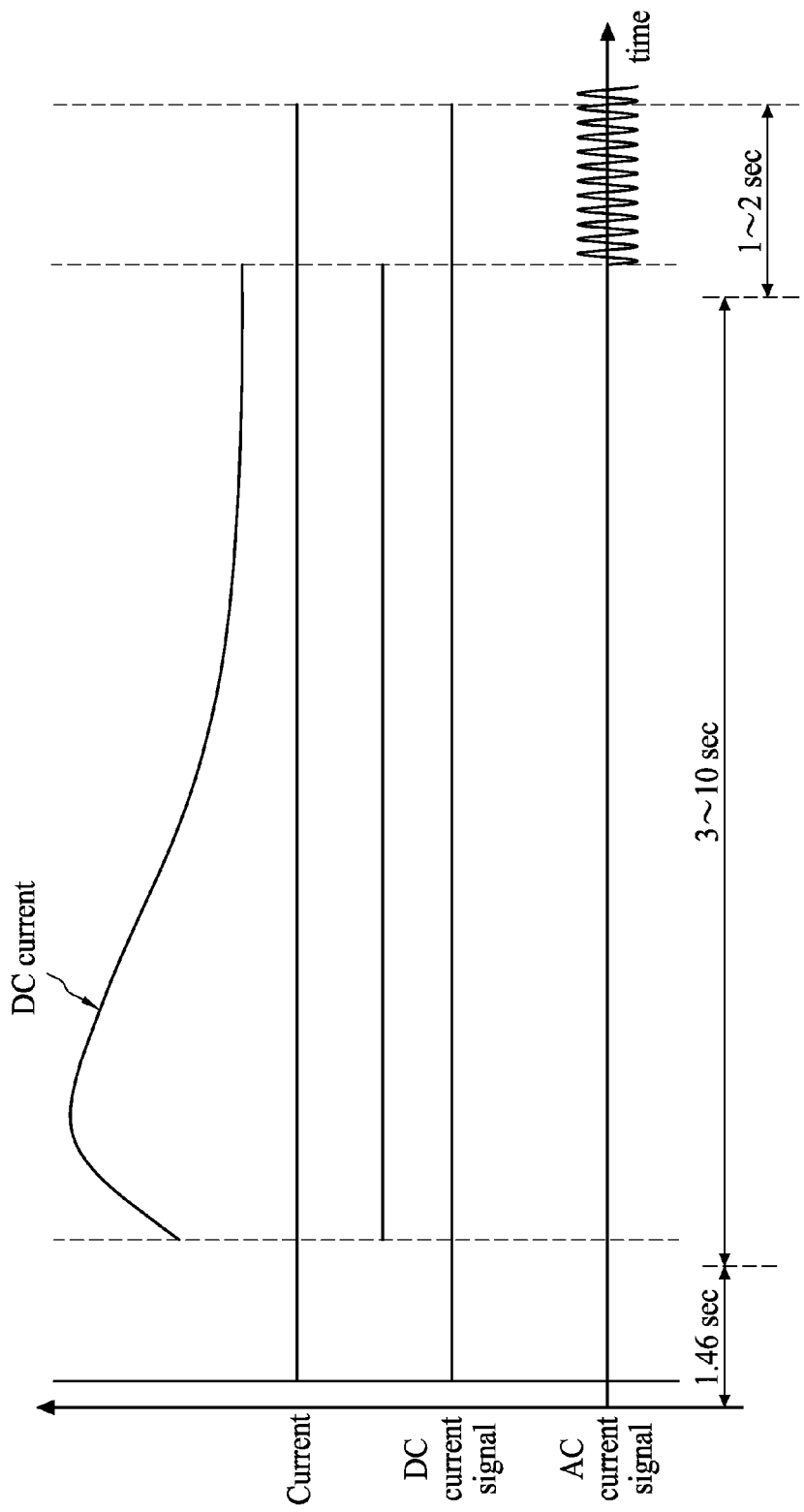
Figure 16:
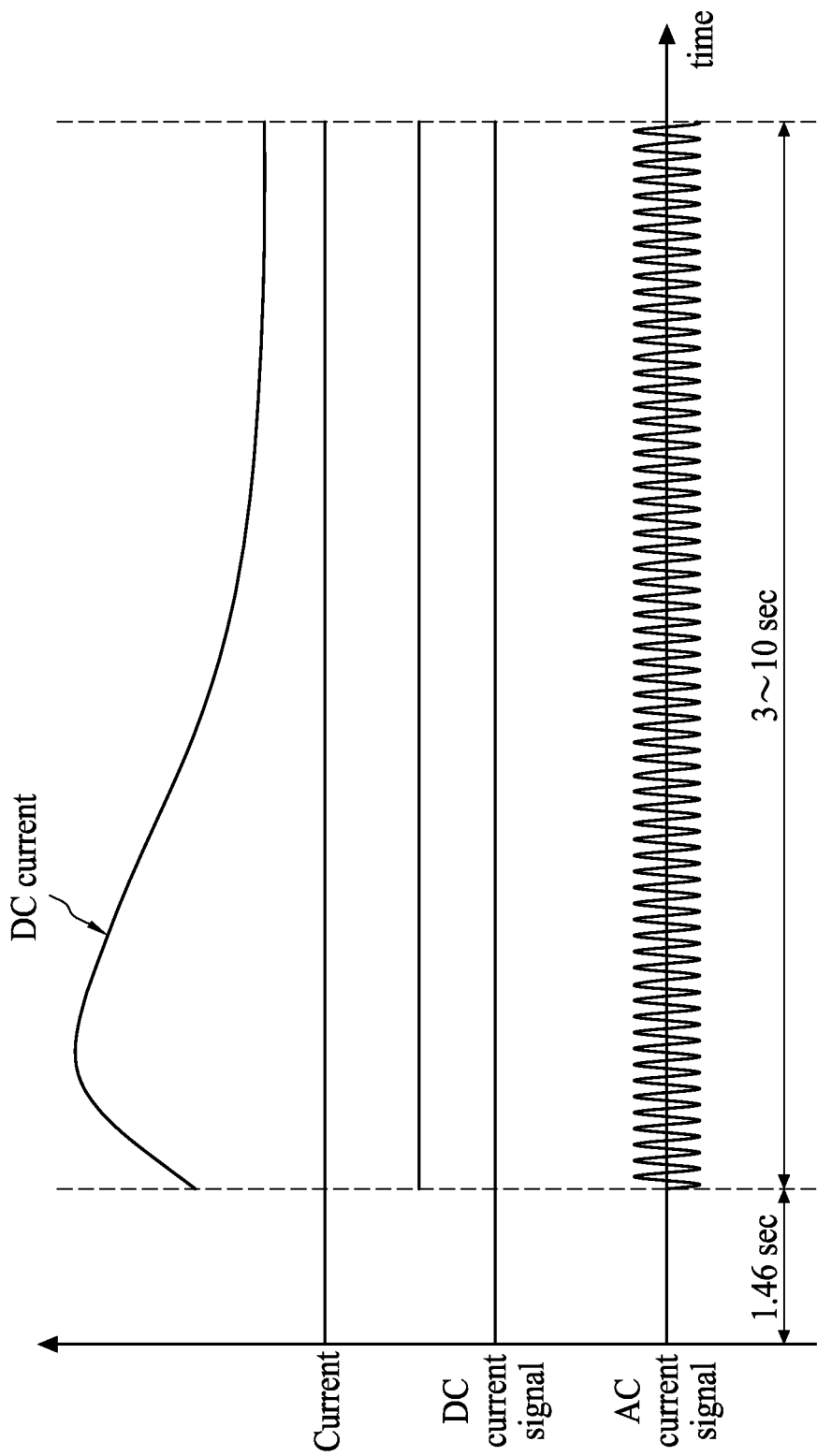
Figure 17:
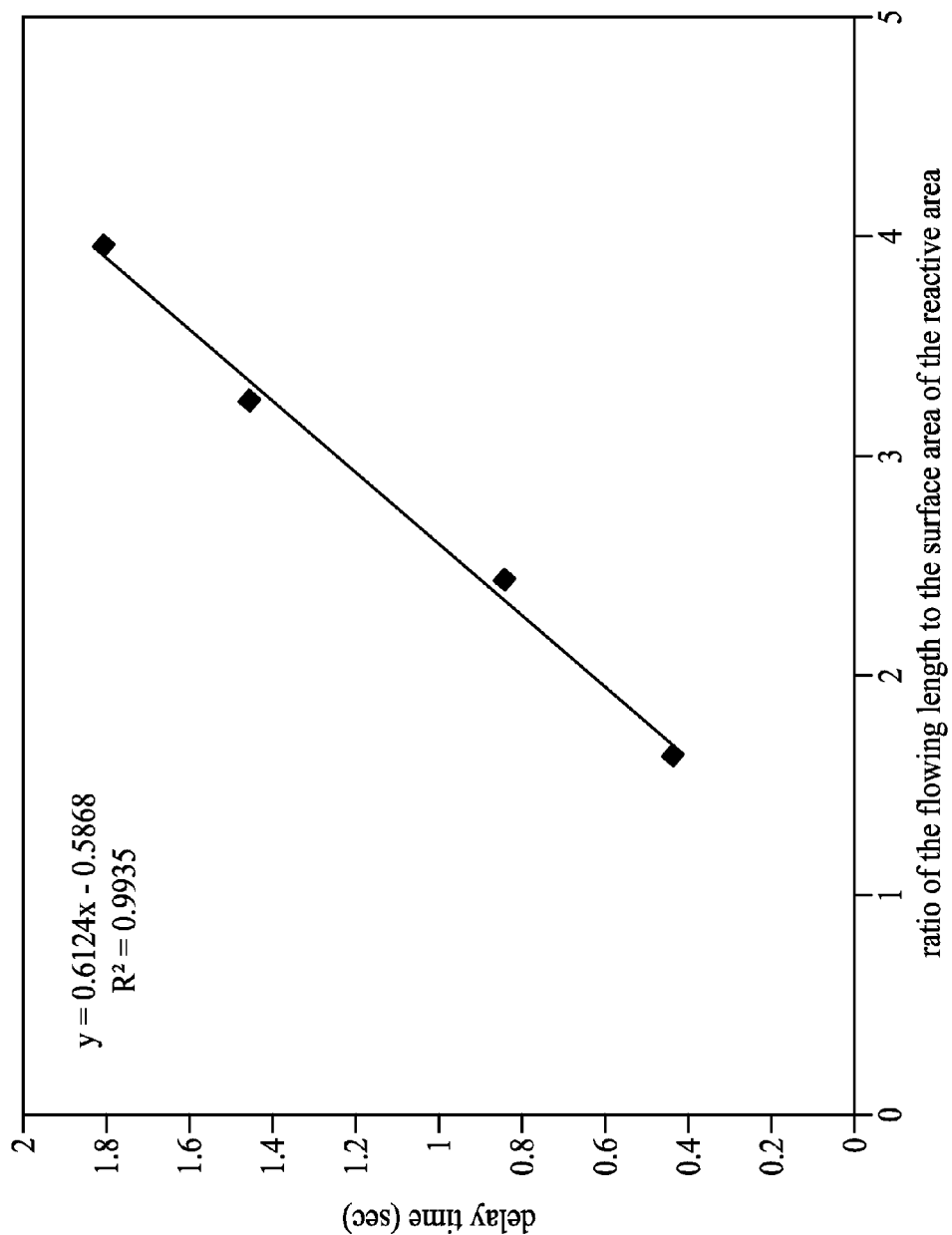
Figure 18:
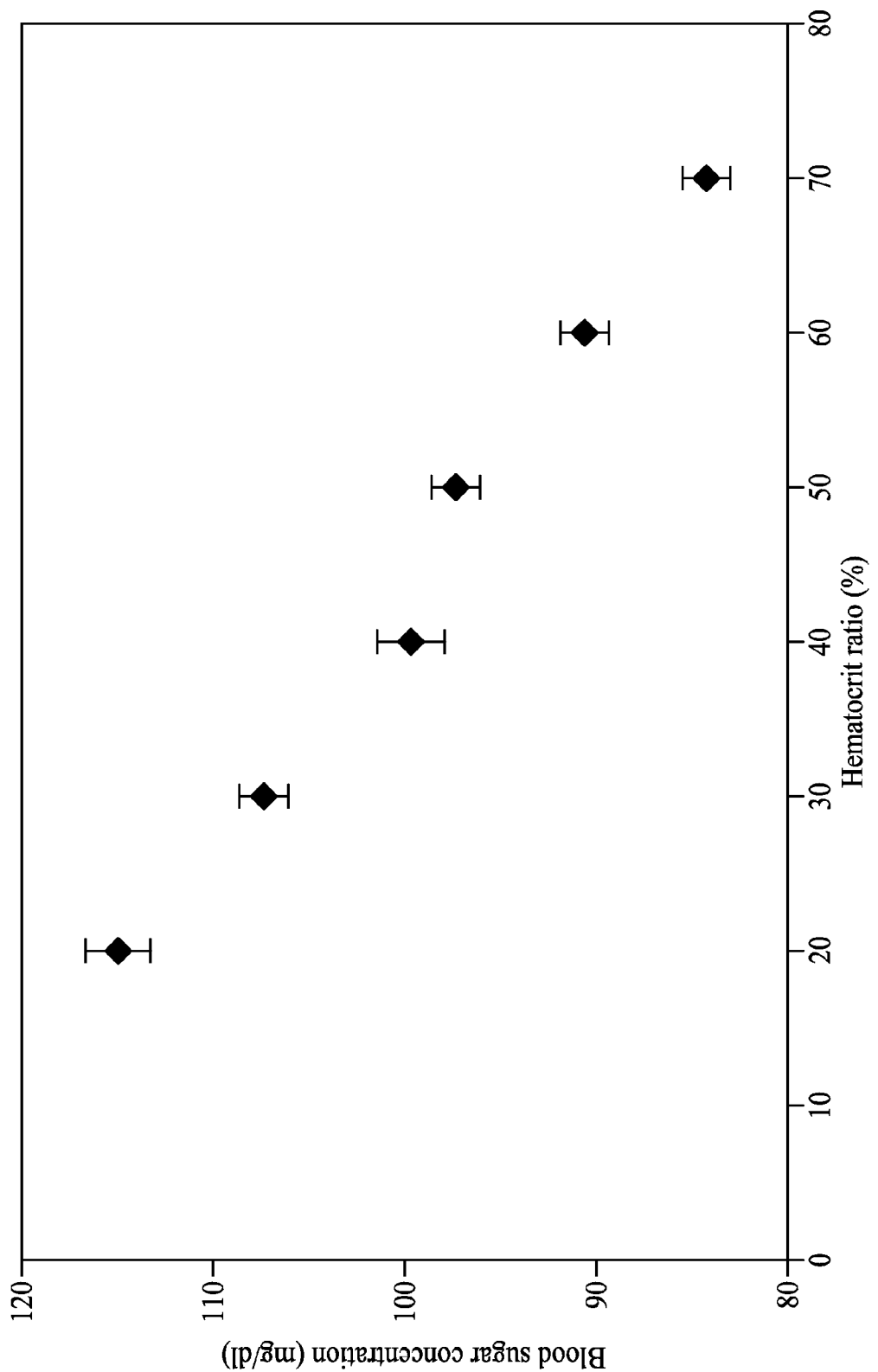
Figure 19:
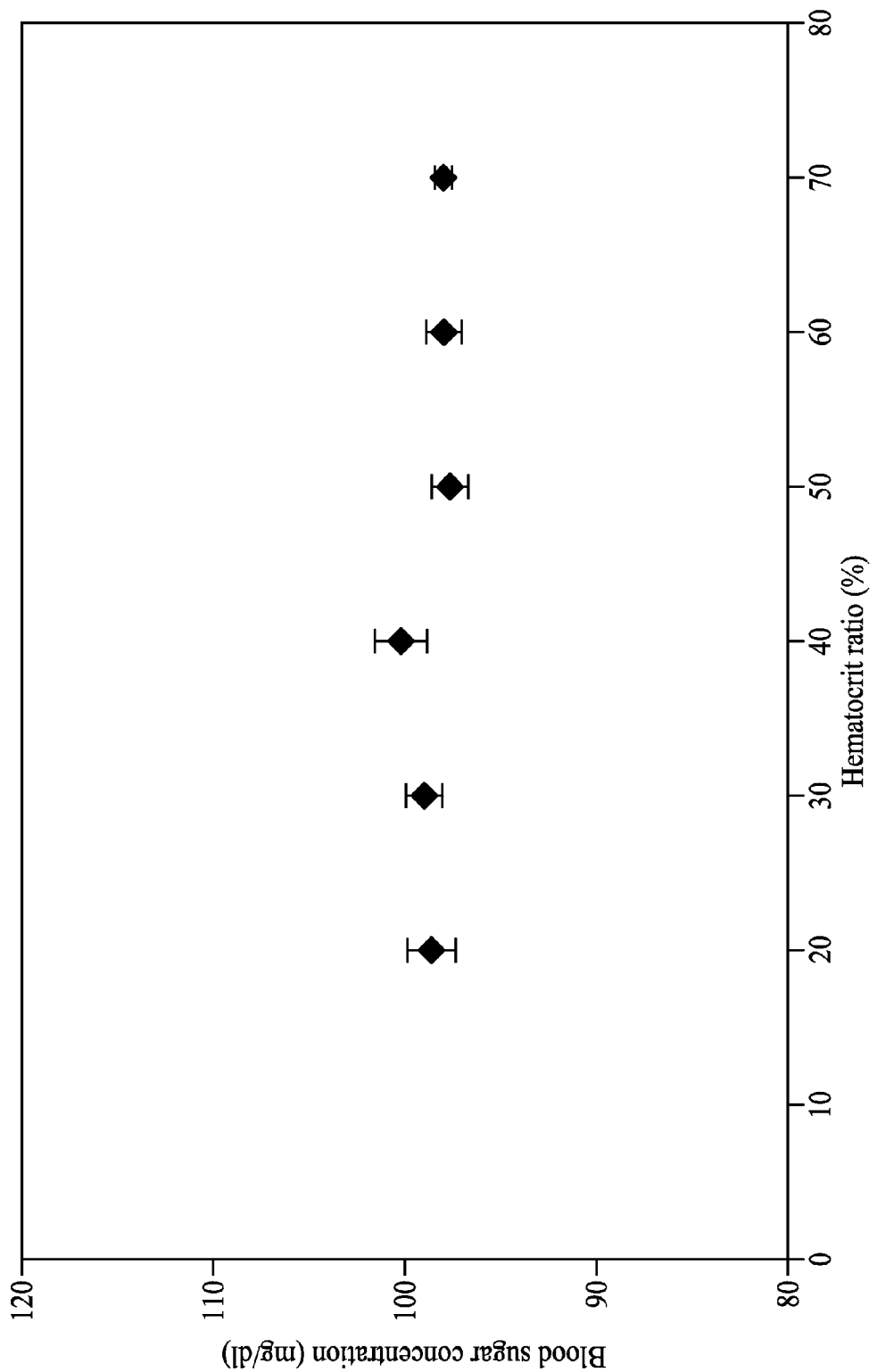
Figure 20:
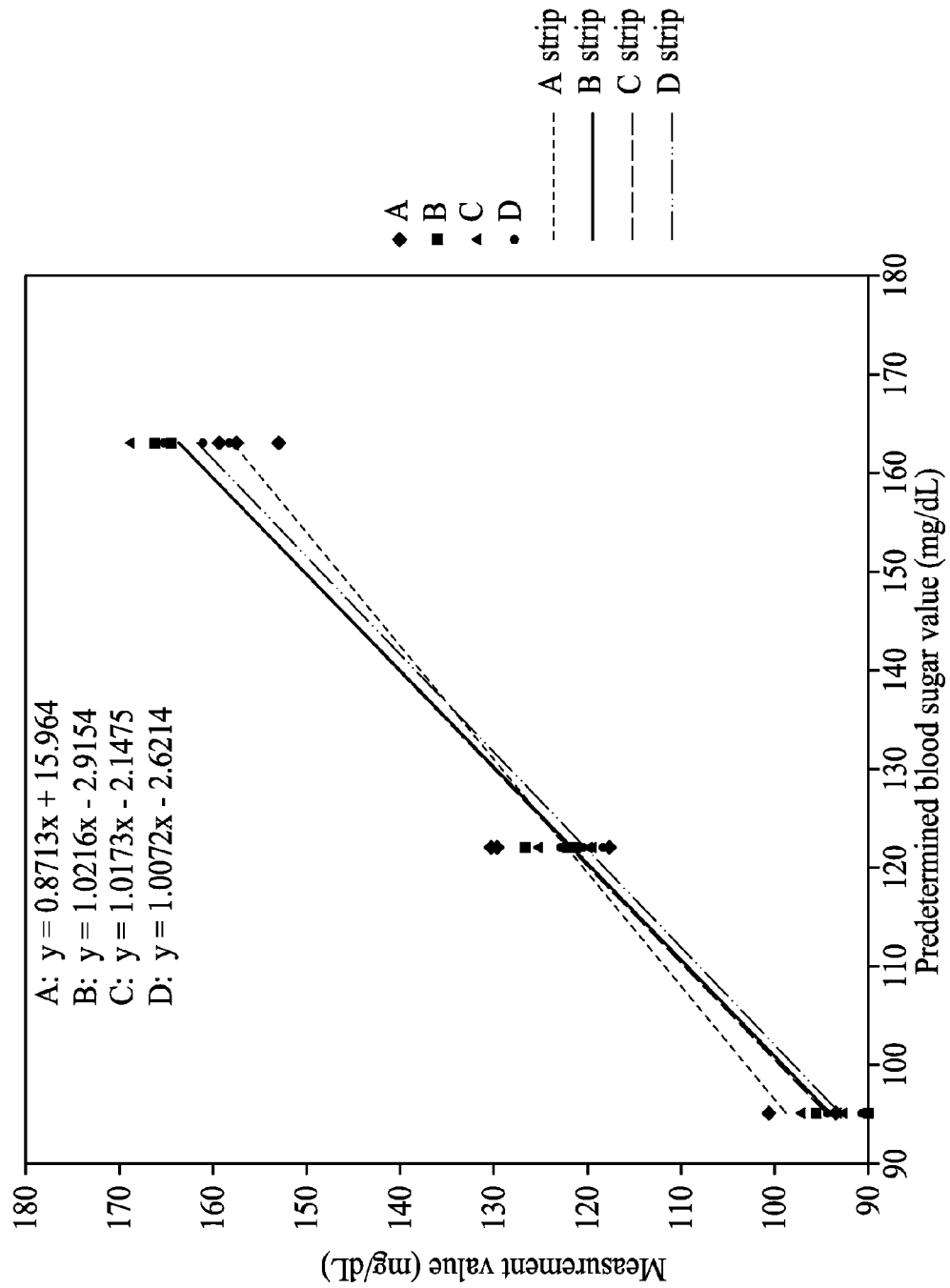

A more complete understanding of the present disclosure may be derived by referring to the detailed description and claims when considered in connection with the Figures, where like reference numbers refer to similar elements throughout the Figures, and:

FIG. 1 is a schematic view of an electrode strip in accordance with an embodiment of the present disclosure;

FIG. 2 is an enlarged view of a groove of an insulation layer in accordance with the embodiment of the present disclosure as in FIG. 1;

FIG. 3 is a cross-sectional view of the electrode strip along the cross-sectional line 1-1 in accordance with the embodiment of the present disclosure as in FIG. 1;

FIG. 4 is a top view of the groove of the insulation layer in accordance with another embodiment of the present disclosure;

FIG. 5 is a top view of a vent-hole of a cover in accordance with another embodiment of the present disclosure;

FIG. 6 is a top view of the groove of the insulation layer in accordance with another embodiment of the present disclosure;

FIG. 7 is a top view of the groove of the insulation layer in accordance with another embodiment of the present disclosure;

FIG. 8 is a cross-sectional view of a groove of the insulation layer in accordance with another embodiment of the present disclosure as in FIG. 7;

FIG. 9 is a top view of the groove of the insulation layer in accordance with another embodiment of the present disclosure;

FIG. 10 illustrates a schematic view of a sensor strip in accordance with another embodiment of the present disclosure;

FIG. 11 illustrates an enlarged view of an opening of the sensor strip in accordance with another embodiment of the present disclosure;

FIG. 12 illustrates a cross-sectional view of the sensor strip along with the cross-sectional line 2-2 in accordance with another embodiment of the present disclosure as in FIG. 11;

FIG. 13 illustrates a cross-sectional view of the sensor strip along with the cross-sectional line 3-3 in accordance with another embodiment of the present disclosure as in FIG. 11;

FIG. 14 illustrates a schematic view of an electric signal of the first experimental procedure in accordance with another embodiment of the present disclosure;

FIG. 15 illustrates a schematic view of an electric signal of the second experimental procedure in accordance with another embodiment of the present disclosure;

FIG. 16 illustrates a schematic view of an electric signal of the third experimental procedure in accordance with another embodiment of the present disclosure;

FIG. 17 illustrates a schematic view of a correlation between a flowing length and the delay time in accordance with another embodiment of the present disclosure;

FIG. 18 illustrates a schematic view of data of blood sugar before hematocrit correction in accordance with another embodiment of the present disclosure;

FIG. 19 illustrates a schematic view of data of blood sugar after hematocrit correction in accordance with another embodiment of the present disclosure; and FIG. 20 illustrates a schematic view of a correlation between values of measured blood sugar and predetermined blood sugar in accordance with another embodiment of the present disclosure.

DETAILED DESCRIPTION

The present disclosure is directed to an electrode strip and a sensor strip including two reactive areas. When a major reactive area measures the analyte concentration, the measured data from the minor is reactive area is used to correct the analyte concentration of the major reactive area so as to obtain a more accurate analyte concentration in the electrode strip and the sensor strip.

In accordance with an embodiment of the present disclosure, when the major reactive area is configured to measure blood sugar, the minor reactive area is configured to detect an interfering factor for correcting the readings of blood sugar. The interfering factor is selected from, but not limited to, hematocrit, triglyceride, cholesterol, uric acid, maltose, galactose, ascorbic acid, acetaminophenol, L-3,4-dihydroxyphenylalanine (L-Dopa) and dopamine.

In accordance with another embodiment of the present disclosure, when the major reactive area is configured to measure cholesterol, the minor reactive area is configured to detect an interfering factor for correcting the readings of cholesterol. Such an interfering factor is selected from, but not limited to, hematocrit, hemoglobin, ascorbic acid, and methyl-3,4-dihydroxyphenylalanine (Methyl-Dopa).

In accordance with another embodiment of the present disclosure, when the major reactive area is configured to measure uric acid, the minor reactive area is configured to detect an interfering factor for correcting the readings of uric acid. Such an interfering factor is selected from, but not limited to, hematocrit, hemoglobin, bilirubin and methyl-3, 4-dihydroxyphenylalanine (Methyl-Dopa).

In accordance with another embodiment of the present disclosure, when the major reactive area is configured to measure hemoglobin, the minor reactive area is configured to detect an interfering factor for correcting the readings of hemoglobin. Such an interfering factor is selected from, but not limited to, hematocrit.

In accordance with another embodiment of the present disclosure, when the major reactive area is configured to measure lactic acid, the minor reactive area is configured to detect an interfering factor for correcting the readings of lactic acid. Such an interfering factor is selected from, but not limited to, hematocrit, ascorbic acid, acetaminophenol and dopamine.

The so-called "substrate" in the present disclosure refers to a thin-layered plate with a flat surface and electric insulating properties. More preferably, the insulating substrate is selected from, but not limited to, the group consisting of polyvinyl chloride (PVC) plates, fiber glass (FR-4) plates, polyester sulphone, bakelite plates, polyester (PET) plates, polycarbonate (PC) plates, glass plates and ceramic plates (CEM-1). Particularly, a thickness of the substrate ranges from about 0.03 mm to about 0.7 mm, from about 0.07 mm to about 0.15 mm, or from about 0.5 mm to about 0.62 mm.

The so-called "electrode set" or "electrode layer" in the present disclosure includes at least two metal electrodes that are isolated and disconnected from each other and used to connect the electric current biosensor. According to the preferred embodiment of the present disclosure, either the electrode set or the electrode layer is partly covered by an electric insulating layer. An end of both metal electrodes is exposed by the electric insulation layer, which includes a working electrode and a reference electrode, and the other end of which forms connections of the working electrode and the reference electrode. The connections are used to connect the sensor, while the electric effect is induced during the electrochemical reaction caused by the analyte and the aforementioned sensor. More preferably, the components used in the electrode layer or the electrode set can include carbon paste, gold paste, silver paste, mixed carbon-silver paste, evaporated graphite or copper paste, or a combination thereof (e.g., screen printing of silver paste initially, followed by printing of carbon paste), or any conductive paste material that is suitable for screen printing and can be dried at below 80° C.

The so-called "insulation layer" and "reactive layer" in the present disclosure refers to a thin layer formed by a material with electric insulating properties and partially covering the electrode set or the electrode layer. According to a preferable embodiment of the present disclosure, the electric insulation layer does not cover the reaction zone and the connections of the electrode set or the electrode layer, and is formed on the substrate. Accordingly, the material of the insulation layer is selected from, but not limited to, PVC insulation tape, PET insulation tape, thermal curing adhesive and ultraviolet photo-curable adhesive. More preferably, the insulation layer has a thickness from about 0.01 mm to about 0.6 mm, from about 0.4 to about 0.51 mm, or from about 0.02 to about 0.03 mm. In addition, a thickness of the reactive layer is from about 0.51 mm to about 1.1 mm, from about 0.9 mm to about 1.51 mm, and from about 0.72 mm to is about 2.03 mm.

The present invention is directed to an electrode strip, a sensor strip and a system thereof. In order to make the present disclosure completely comprehensible, detailed steps and structures are provided in the following description. Obviously, implementation of the present disclosure does not limit special details known by persons skilled in the art. In addition, known structures and steps are not described in details, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed embodiments, and is defined by the claims.

The following description of the disclosure accompanies drawings, which are incorporated in and constitute a part of this specification, and illustrate embodiments of the disclosure, but the disclosure is not limited to the embodiments. In addition, the following embodiments can be properly integrated to complete another embodiment.

References to "one embodiment," "an embodiment," "other embodiments," "another embodiment," etc. indicate that the embodiment(s) of the disclosure so described may include a particular feature, structure, or characteristic, but not every embodiment necessarily includes the particular feature, structure, or characteristic. Further, repeated use of the phrase "in the embodiment" does not necessarily refer to the same embodiment, although it may.

Unless specifically stated otherwise, as apparent from the following discussions, it is appreciated that throughout the specification discussions utilizing terms such as "measuring," "receiving," "calculating," "correcting," "detecting," or the like, refer to the action and/or processes of a computer or computing system, or similar electronic computing device, state machine and the like that manipulate and/or transform data represented as physical, such as electronic, quantities into other data similarly represented as physical quantities.

In addition, unless specifically stated otherwise, as apparent from claims and detailed description, it is appreciated that throughout the specification the quantity of components is single. If the quantity of the labeled component is one, the quantifier is explained to include one unit or at least one unit. If the quantity of the labeled component is a plurality, the quantifier is explained to include at least two units.

FIG. 1 illustrates a schematic view of an electrode strip 10 in accordance with an embodiment of the present disclosure. The electrode strip 10 includes a substrate 100, an electrode layer 110, an insulation layer 120, and a cover 130.

In some embodiments as in FIG. 1, the material of the substrate 100 is a polyvinylchloride (PVC) plate, but is not limited to such. The electrode layer 110 is disposed on the substrate 100. In the specification and patent scope, the term "on" means that a first member is directly or indirectly disposed above the second member. For instance, the sentence that the electrode layer 110 is disposed on the substrate 100 means two embodiments. The first embodiment means that the electrode layer 110 is directly disposed on the substrate 100. The second embodiment means that the electrode layer 110 is indirectly disposed above the substrate 100. The term "indirectly" means that in vertical view, two members are disposed at upper position and lower position, respectively, while other objects, material layers or gaps are disposed between the two members.

The electrode layer 110 includes a first electrode set 111 and a second electrode set 112. In the embodiment, the electrode layer 110 further includes adhesive, which is used to fix the electrode layer 110 on the substrate 100 or the insulation layer 120.

In the embodiment shown in FIG. 1, the insulation layer 120 includes a groove 121, a first protrusion 122 and a second protrusion 123.

As shown in FIG. 1, the groove 121 includes a first long side 124 and a second long side 125. The first long side 124 is disposed at a lateral edge of the groove 121, while the second long side 125 is disposed at the other lateral edge of the groove 121. In other words, the first long side 124 is a lateral wall of the groove 121, but is not limited to such, while the second long side 125 is the other lateral wall of the groove 121, but is not limited to such. In the embodiment, the first protrusion 122 is configured to perpendicularly extend from the first long side 124 toward the groove 121, while the second protrusion 123 is configured to perpendicularly extend from the second long side 125 toward the groove 121. However, in other embodiments (not shown), there is no need for the first protrusion 122 to be perpendicular to the first long side 124. In other words, the first protrusion 122 and the first long side 124 form an included angle. Similarly, there is no need for the second protrusion 123 to be perpendicular to the second long side 125.

In the embodiment shown in FIG. 1, the first protrusion 122 and the second protrusion 123 divide the groove 121 into a first reactive area 140 and a second reactive area 150. The first electrode set 111 is disposed in response to the first reactive area 140. In other words, the first electrode set 111 is disposed on the substrate 100 in relation to the first reactive area 140. Similarly, the second electrode set 112 is disposed in response to the second reactive area 150. In other words, the second electrode set 112 is disposed on the substrate 100 in relation to the second reactive area 150.

In the embodiment, the cover 130 is disposed on the insulation layer 120 and includes a vent-hole 131 which is connected with the groove 121. Thus, when the sample liquids flow into the groove 121, the vent-hole 131 enables the gaseous molecules inside the groove 121 to exhaust.

In the embodiment shown in FIG. 1, the electrode layer 110 further includes a third electrode set 113, which is disposed in response to the second reactive area 150. In other words, the third electrode set 113 is disposed on the substrate 100 in relation to the second reactive area 150. Particularly, the third electrode set 113 is disposed adjacent to an end 126 of the groove 121. In other words, the third electrode set 113 is disposed far away from an aperture 127 of the groove 121. By such design, it is useful to detect whether the sample liquids flow over the surface of the groove 121 or whether the sample liquids have reacted with the first electrode set 111 and the second electrode set 112. In other embodiments (not shown), several identification electrodes used to perform other functions are provided in the present disclosure so as to confirm whether the electrode strip is appropriately connected with a sensor (not shown).

As shown in FIG. 1, the insulation layer 120 is disposed on the electrode layer 110 and exposes a reaction zone 114 of the first electrode set 111, the second electrode set 112 and the third electrode set 113. The connections of the reaction zone 114 are configured to be electrically connected to the sensor (not shown). In other words, the insulation layer 120 does not cover the reaction zone 114 of the electrode layer 110.

FIG. 2 is an enlarged view of FIG. 1. In the embodiment shown in FIG. 2, the first protrusion 122 and the second protrusion 123 extend from opposing sides. Since the first protrusion 122 and the second protrusion 123 extend toward each other, a portion of the first protrusion 122 and a portion of the second protrusion 123 are overlapped within a certain view. The overlapped portion has a distance, which is called an overlapped distance D1. If the insulation layer 120 further includes a third protrusion (not shown), the overlapped distance of the third protrusion is defined in accordance with the previous overlapped distance D1 and the overlapped portion between the third protrusion and the protrusion (either the first is protrusion or the second protrusion) adjacent to the third protrusion.

As shown in FIG. 2, the first protrusion 122 and the second protrusion 123 form a gap D2. In the embodiment, the gap D2 is from about 0.1 mm to about 1.3 mm. In the embodiment, a first length includes a length of a short side D3 of the first protrusion 122, a length of the gap D2, and a length of a short side D4 of the second protrusion 123. A ratio of the first length to a length of either the first long side 124 or the second long side 125 is from about 5% to about 30%. In addition, a ratio of a length of a long side D6 of the first protrusion 122 to a length of a short side D8 of the groove 121 is from about 60% to about 90%, or a ratio of a length of a long side D7 of the second protrusion 123 to the length of a short side D8 of the groove 121 is from about 60% to about 90%.

In the embodiment shown in FIGS. 1 and 2, when the first protrusion 122 and the second protrusion 123 are disposed adjacent to the end 126 of the groove 121, a surface area of the first reactive area 140 is larger than a surface area of the second reactive area 150. In other embodiments (not shown), when the first protrusion 122 and the second protrusion 123 are disposed adjacent to the aperture 127 of the groove 121, the surface area of the first reactive area 140 is smaller than the surface area of the second reactive area 150.

In some embodiments, a flowing length L includes the length of the long side D6 of the first protrusion 122, the length of the short side D3 of the first protrusion 122, the length of the overlapped distance D1, the length of the short side D4 of the second protrusion 123, and the length of the long side D7 of the second protrusion 123. In is other embodiments (not shown), if the electrode strip 10 further includes a third protrusion (not shown), a flowing length L' further includes a length of a long side and a short side of the third protrusion and a length of an overlapped distance between the third protrusion and either the first protrusion 122 or the second protrusion 123. Therefore, the flowing length L' is larger than the flowing length L. In the embodiment, the flowing length L is from about 0.9 mm to about 1.8 mm.

In addition, as the flowing length L extends, the period of time (or delay time) in which it takes for the sample liquids to flow into the second reactive area 150 through the flowing length L will increase. In other words, the flowing length L is configured to postpone the sample reaching the second reactive area 150 from the first reactive area 140 so as to generate a delay time. The delay time is from about 0.4 sec to about 2.0 sec.

FIG. 3 is a cross-sectional view along the cross-sectional line 1-1 of FIG. 1. A bottom of the first protrusion 122 connects with the electrode layer 110 while a top portion of the first protrusion 122 connects with the cover 130. The electrode layer 110 includes the first electrode set 111, the second electrode set 112, the third electrode set 113, and an adhesive 115. However, in other embodiments (not shown), the third electrode set 113 is optional. Particularly, the first protrusion 112 connects on the substrate 100 through the adhesive 115. As shown in FIG. 3, the first protrusion 122 isolates the first reactive area 140 from the second reactive area 150 shown in FIG. 1. Similarly, is a bottom of the second protrusion 123 connects with the adhesive 115 of the electrode layer 110 while a top portion of the second protrusion 123 connects with the cover 130. In other embodiments (not shown), the top portion of the first protrusion 122 or the second protrusion 123 connects with the cover 130 through the adhesive (not shown).

In the embodiment shown in FIGS. 1 to 3, the first protrusion 122 is disposed adjacent to the end 126 of the groove 121, while the second protrusion 123 is disposed adjacent to the aperture 127 of the groove 121. In the embodiment shown in FIG. 4, the first protrusion 222 is disposed adjacent to the aperture 227 of the groove 221 while the second protrusion 223 is disposed adjacent to the end 226 of the groove 221. In the embodiment shown in FIG. 4, since the first protrusion 222 divides the groove 221 into a first reactive area 240 and a second reactive area 250 through the connection between the cover (not shown) and the electrode layer (not shown), the second protrusion 223 is not necessary to connect with the cover; hence, the second protrusion 223 does not separate the first reactive area 240 from the second reactive area 250. As shown in FIGS. 2 and 3, after the sample liquids flow into the gap D2 between the first protrusion 122 and the second protrusion 123, the gap D2 is not necessarily full of the sample liquids. Thus, the protrusion disposed adjacent to the end 126 of the groove 121 is not necessary to connect with the cover 130 in order to separate the first reactive area 240 from the second reactive area 250.

In the embodiment shown in FIGS. 1 to 3, when the stream of the sample liquids flows into the groove 121, the first protrusion 122 and the second protrusion 123 become obstacles that alter the direction is of the sample liquids flowing into the groove 121. The flowing direction of the sample liquids in the gap D2 is perpendicular to the flowing direction of the sample liquids flowing into the groove 121. In other words, the first protrusion 122 and the second protrusion 123 are configured to alter the direction of the sample liquids flowing into the groove.

Referring to FIGS. 1 to 3, the vent-hole 131 connects with the second reactive area 150. After the sample liquids flow into the groove 121, the vent-hole 131 becomes useful in exhausting the gaseous molecules inside the groove 121. Thus, the vent-hole 131 is configured to generate a capillary attraction which drive the sample liquids to flow into the second reactive area 150 from the first reactive area 140. However, in other embodiment as shown in FIG. 5, the vent-hole 213 is disposed to connect with the first reactive area (not shown).

In addition, as shown in FIG. 6, the embodiments of FIGS. 1 to 3 further include a third protrusion 128, which is disposed adjacent to the second protrusion 123. As shown in FIG. 7, the third protrusion 128 is disposed adjacent to the first protrusion 122. FIG. 8 is a cross-sectional view of FIG. 7. The sample liquids have to pass through the first protrusion 122, the second protrusion 123, and the third protrusion 128 in order to reach the second reactive area 150.

Moreover, the electrode strip 10 further includes a fourth protrusion 329 as shown in FIG. 9. The first protrusion 322, the second protrusion 323, the third protrusion 328 and the fourth protrusion 329 may further increase the flowing length so as to increase the delay is time.

As shown in FIG. 10, the sensor strip 40 of the present disclosure includes a substrate 400, an electrode layer 410 and a reactive layer 420.

In the embodiment, the electrode layer 410 is disposed on the substrate 400 and includes a first electrode set 411 and a second electrode set 412.

As shown in FIG. 10, the electrode layer 410 further includes a third electrode set 413, which is disposed adjacent to the second electrode set 412.

In the embodiment shown in FIG. 10, the reactive layer 420 includes an opening 421, a first protrusion 422, a second protrusion 423 and a vent-hole 424.

The first protrusion 422 is disposed at a wall of the opening 421 and extends toward the opening 421 while the second protrusion 423 is disposed at a wall of the opening 421 and extends toward the opening 421. In particular, the first protrusion 422 perpendicularly extends from the long side 425 of the opening 421 toward the opening 421 while the second protrusion 423 perpendicularly extends from the long side 426 of the opening 421 toward the opening 421. However, in another embodiment (not shown), the first protrusion 422 is not necessary to be perpendicular to the long side 425 of the opening 421. In other words, the first protrusion 422 and the long side 425 of the opening 421 form an included angle. Similarly, the second protrusion 423 is not necessary to be perpendicular to the long side 426 of the opening 421.

As shown in FIG. 10, the first protrusion 422 and the second protrusion 423 divide the opening 421 into a first reactive area 440 and a second reactive area 450. The first electrode set 411 is disposed in response to the first reactive area 440 while the second electrode set 412 is disposed in response to the second reactive area 450. In addition, the third electrode set 413 is disposed in response to the second reactive area 450 and is adjacent to an end 427 of the opening 421. Thus, the third electrode set 413 is configured to detect whether the sample liquids flow over the surface of the opening 421.

In the embodiment, the vent-hole 424 connects with the opening 421. When the sample liquids flow into the opening 421, the vent-hole 424 is then allowed to exhaust the gaseous molecules inside the opening 421.

As shown in FIG. 10, the reactive layer 420 is disposed on the electrode layer 410 and exposes the reaction zone 414 of the first electrode set 411, the second electrode set 412 and the third electrode set 413. The connection of the reaction zone 414 is electrically connected with a sensor (not shown). In other words, the reactive layer 420 does not cover the reaction zone 414 of the electrode layer 410.

FIG. 11 is an enlarged view of FIG. 10. In the embodiment shown in FIG. 11, the first protrusion 422 and the second protrusion 423 extend from opposing sides. Since the first protrusion 422 and the second protrusion 423 extend toward each other, a portion of the first is protrusion 422 and a portion of the second protrusion 423 are overlapped. The distance of the overlapped portion is defined as an overlapped distance D9. If the reactive layer 420 further includes a third protrusion (not shown), the overlapped distance is defined in accordance with the previous discussed distance D9 and a distance overlapped between the third protrusion and the protrusion (either the first protrusion 422 or the second protrusion 423) adjacent to the third protrusion.

As shown in FIG. 11, the first protrusion 422 and the second protrusion 423 form a gap D10. In the embodiment, the gap 10 is from about 0.1 mm to about 1.3 mm. In addition, a second length includes a length of a short side D11 of the first protrusion 422, a length of the gap D10 and a length of a short side D12 of the second protrusion 423. A ratio of the second length to either a length D13 of the long side 425 of the opening 421 or a length D13 of the long side 426 of the opening 421 is from about 5% to about 30%. Furthermore, a ratio of a length of the short side D16 of the opening 421 to either a length of the long side D14 of the first protrusion 422 or a length of the long side D15 of the second protrusion 423 is from about 1.111 to about 1.666. In some embodiments for utilizing laser ablation techniques, a ratio of the length of the short side D11 of the first protrusion 422 to the length of the long side D13 of the opening 421 is from about 0.05 to about 0.3. In certain embodiments for utilizing mechanical cutting techniques, a ratio of the length of the short side D11 of the first protrusion 422 to the length of the long side D13 of the opening 421 is from about 0.1 to is about 0.3.

In the embodiment, the flowing length S includes the length of the long side D14 of the first protrusion 422, the length of the short side D11 of the first protrusion 422, the length of the overlapped distance D9, the length of the short side D12 of the second protrusion 423 and the length of the long side D15 of the second protrusion 423. In other embodiments (not shown), if the sensor strip 40 further includes a third protrusion (not shown), a flowing length S' further includes a length of the long side of the third protrusion, the short side of the third protrusion and an overlapped distance between the third protrusion and either the first protrusion 422 or the second protrusion 423. Thus, the flowing length S' is larger than the flowing length S. In some embodiments, the flowing length S is from about 0.9 mm to about 1.8 mm.

As the flowing length S extends, the period of time in which it takes for the sample liquids to reach the second reactive area 450 through the flowing length S will increase. In other words, the flowing length is configured to postpone the sample liquids reaching the second reactive area 450 from the first reactive area 440 so as to generate a delay time, which is from about 0.4 to about 2.0 seconds.

FIG. 12 is a cross-sectional view along a cross-sectional line 2-2 of FIG. 11. FIG. 13 is a cross-sectional view along a cross-sectional line 3-3 of FIG. 11. A bottom of the first protrusion 422 connects with the electrode layer 410. In particular, the first protrusion 422 is connected on the substrate 400 through the adhesive (not shown) of the electrode layer 410. As shown in FIGS. 10 and 12, the first protrusion 422 divides the opening 421 into a first reactive area 440 and a second reactive area 450. Similarly, as shown in FIG. 13, a bottom of the second protrusion 423 connects with the electrode layer 410.

As shown in FIGS. 12 and 13, the first protrusion 422 is configured to narrow a bore of the opening 421 to form a first inner bore 460. The second protrusion 423 is configured to narrow a bore of the opening 421 to form a second inner bore 470. The first inner bore 460 is located opposite to the second inner bore 470 in relation to the opening 421.

Referring to FIG. 10, the sensor strip 40 further includes a reaction film 480 (indicated by the dotted line). The reaction film 480 is a film covering on the second reactive area 450. The reaction film 480 formulation is added dropwise or printed onto the second reactive area 450. Since the second reactive area 450 includes the reaction film 480, the second electrode set 412 in the second reactive area 450 is configured to measure the analyte concentration in major reactive area as previously discussed. In addition, the second electrode set 412 receives the electric signals through the reaction zone 414 of the second electrode set 412 so as to measure the analyte. The electric signal is, but not limited to, the DC signal, the AC signal, or an AC with DC offset signal.

Moreover, since the first electrode set 411 and the second electrode set 412 are isolated by the first protrusion 422 and the second protrusion 423, the DC signal applied by the second electrode set 412 is not disrupted by the electric signals of the first electrode set 411.

The present disclosure further provides a measurement system with hematocrit correction including the above-mentioned electrode strips, or sensor strips and a sensor.

The first electrode set of the above-identified electrode strips or sensor strips is configured to measure a hematocrit concentration or the concentration of the above-mentioned interfering factors of the minor reactive area. The second electrode set is configured to measure the analyte concentration of the major reactive area. However, in other embodiments, the first electrode set is also configured to measure the analyte concentration of the foresaid major reactive area while the second electrode set is configured to measure a hematocrit concentration or the concentration of interfering factors of the minor reactive area. The first electrode set 411 shown in FIG. 10 receives an electric signal from the reaction zone 414 of the first electrode set 411 and then measures the analyte concentrations or interfering factors as previously discussed. The electric signal is, but not limited to, the AC signal, the DC signal, or the AC with DC offset signal.

The sensor is configured to electrically connect with the electrode strip or the sensor strip and includes a power source, a detector and a microprocessor.

The power source is configured to provide or transmit the AC signal or the DC signal to the first electrode set and the second electrode set.

The detector is configured to detect a first reactive value in response to the hematocrit concentration and a second reactive value in is response to the analyte concentration.

The microprocessor is configured to calculate the hematocrit-corrected analyte concentration in response to the first reactive value and the second reactive value.

Experimental Example

The first experimental procedure (referring to FIG. 14):

The power source provides the AC signal to the first reactive area in about 1 to 2 seconds so as to measure the hematocrit concentration (HCT);

The power source stops applying the signal at about 1.46 seconds to allow the sample liquids, such as blood, to reach the second reactive area through the region consisting of at least one of the protrusions;

The power source resumes to transmit the DC signal to the second reactive area in about 3 to 10 seconds so as to measure the analyte concentration, such as blood sugar value, uric acid value and so on.

The second experimental procedure (referring to FIG. 15):

The power source is turned off at about 1.46 seconds to allow the sample liquids, such as blood, to reach the second reactive area through the region consisting of at least one of the protrusions. Subsequently, the power source resumes to provide the DC signal to the second reactive area in about 3 to 10 seconds so as to measure the analyte concentration, such as blood sugar value, uric acid value and so on.

Subsequently, the power source transmitting the AC signal to the first reactive area takes about 1 to 2 seconds to measure the hematocrit concentration (HCT).

The third experimental procedure (referring to FIG. 16):

The power source is turned off at about 1.46 seconds to allow the sample liquids, such as blood, to reach the second reactive area through the region consisting of at least one of the protrusions. Subsequently, the power source simultaneously provides a DC signal and an AC signal in about 3 to 10 seconds. The AC signal is transmitted to the first reactive area so as to measure the hematocrit concentration (HCT). The DC signal is transmitted to the second reactive area so as to measure the analyte concentration, such as blood sugar value, uric acid value and so on.

Since the surface area of the groove or opening is constant, a correlation between a ratio of the flowing length to the surface area of the reactive area and the delay time of flowing the sample liquids into the second reactive area is shown in FIG. 17, which is depicted in accordance with Table 1 as shown below.

TABLE 1

| Flowing length (mm) | Surface area of reactive area (mm$^2$) | Flowing length/Surface area of reactive area | Delay time (sec.) |
| --- | --- | --- | --- |
| 0.983 | 0.60 | 1.64 | 0.44 |
| 1.025 | 0.42 | 2.44 | 0.85 |
| 1.123 | 0.34 | 3.26 | 1.46 |
| 1.74 | 0.44 | 3.95 | 1.82 |

Because the total surface area of the groove or opening is constant, a decrease in the surface area of the reactive area will result from the extension of the flowing length or increasing number of is protrusions.

The present disclosure measures the sample (such as blood sugar) and a hematocrit concentration in accordance with the first experimental procedure. In certain embodiments, the analyte concentration is measured in accordance with the second experimental processes or the third experimental processes.

The present disclosure utilizes the samples with predetermined hematocrit concentrations for pre-testing. These samples includes six test samples having hematocrit concentrations of 20%, 30%, 40%, 50%, 60% and 70%, respectively. Each test sample contains a blood sugar amount of 101 mg/dL, and is analyzed by triple measurements as shown in Table 2 below.

TABLE 2

| Hematocrit % | Measured values of blood sugar | | | Mean | Standard deviation |
| --- | --- | --- | --- | --- | --- |
| 20 | 115 | 117 | 113 | 115.0 | 1.63 |
| 30 | 107 | 109 | 106 | 107.3 | 1.25 |
| 40 | 99 | 98 | 102 | 99.7 | 1.70 |
| 50 | 97 | 96 | 99 | 97.3 | 1.25 |
| 60 | 92 | 91 | 89 | 90.7 | 1.25 |
| 70 | 86 | 83 | 84 | 84.3 | 1.25 |

FIG. 18 is depicted in accordance with Table 2 and illustrates the hematocrit concentrations before hematocrit correction. As shown in FIG. 18, the measured values of the blood sugar in these test samples are different and distinguish from the predetermined blood sugar value (101 mg/dL). The measured values of Table 2 are calculated in response to the DC signal and are not corrected in accordance with hematocrit concentrations.

The present disclosure utilizes the hematocrit concentrations measured by the AC signals to correct the above-mentioned values of blood sugar. The hematocrit-corrected blood sugar values are shown in Table 3 below.

TABLE 3

| Hematocrit % | Corrected values of blood sugar | | | Mean | Standard deviation |
|---|---|---|---|---|---|
| 20 | 98 | 99 | 101 | 99.33 | 1.25 |
| 30 | 101 | 99 | 99 | 99.67 | 0.94 |
| 40 | 99 | 102 | 102 | 101.00 | 1.41 |
| 50 | 97 | 99 | 99 | 98.33 | 0.94 |
| 60 | 100 | 98 | 98 | 98.67 | 0.94 |
| 70 | 99 | 98 | 99 | 98.67 | 0.47 |

FIG. 19 is depicted in accordance with Table 3 and illustrates the hematocrit-corrected values of blood sugar. As shown in FIG. 19, after the blood sugar values of the six test samples are corrected according to hematocrit concentrations, the mean of the blood sugar values falls within the range of 101±3 mg/dL.

The flowing length (from 1.1 mm to 1.5 mm) of the electrode strip or sensor strip is designed to reduce the coefficient of variation of blood sugar values.

The present disclosure utilizes four strips (indicated by A, B, C and D), which have different flowing lengths and their own delay times. Nine test samples with predetermined hematocrit concentrations and predetermined blood sugar values are tested in triple measurements as shown in Table 4 below.

TABLE 4

| Symbol | Flowing length (mm) | Delay time | Predetermined blood sugar (mg/dL) | Hematocrit % | | | | | | | | |
|---|---|---|---|---|---|---|---|---|---|---|---|---|
| | | | | 30 | | | 40 | | | 50 | | |
| | | | | 95 | 122 | 163 | 95 | 122 | 163 | 95 | 122 | 163 |
| A | 0.983 | 0.44 | Measured values (mg/dL) | 94.67 | 130.33 | 159.33 | 94.33 | 117.67 | 157.33 | 100.67 | 129.67 | 153.00 |
| B | 1.025 | 0.85 | | 94 | 122 | 158 | 95.67 | 126.67 | 164.67 | 90 | 121 | 166.33 |
| C | 1.123 | 1.46 | | 97.33 | 120 | 157.67 | 93.67 | 125.33 | 169 | 93 | 119.67 | 164.67 |
| D | 1.74 | 1.82 | | 93.67 | 118.33 | 158.33 | 94.33 | 120.67 | 165 | 90.67 | 122.67 | 161 |

FIG. 20 is depicted in accordance with Table 4 and illustrates the correlation between the measured values of the blood sugar and the predetermined blood sugar. The coefficient of variation of data among strips A to D are 0.062, 0.07, 0.03 and 0.05, respectively. As shown in FIG. 20, when the flowing length is designed to be close to 1.123 mm (the flowing length of the C strip), the coefficient of variation is minimized. Thus, in order to increase the accuracy, the flowing length is designed to range from about 1.1 mm to about 1.5 mm.

In the present disclosure, the sensor strip and the electrode strip provide simple operations, low cost requirements and avoid cross-contamination of sample liquids in two reactive areas so as to be suitable for domestic usage and quick diagnosis. Although the present disclosure is disclosed in the above-identified embodiments, which do not limit the present disclosure, persons having ordinary skill in the art, is without departing from the spirit and scope of the present disclosure, may modify or amend accordingly. Therefore, the protection scope of the present disclosure is based on the appended claims.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, and composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may m be utilized according to the present disclosure. Accordingly, the appended claims are intended to include within their scope such processes, machines, manufacture, compositions of matter, means, methods, or steps.

What is claimed is:

1. An electrode strip, comprising:
   a substrate;
   an electrode layer disposed on the substrate, wherein the electrode layer includes a first electrode set and a second electrode set;
   an insulation layer including a groove, a first protrusion and a second protrusion, wherein the groove includes a first long side and a second long side, the first protrusion is configured to extend from the first long side toward the groove, the second protrusion is configured to extend from the second long side toward the groove, the first protrusion and the second protrusion divide the groove into a first reactive area and a second reactive area, the first electrode set is disposed in response to the first reactive area, and the second electrode set is disposed in response to the second reactive area; and
   a cover including a vent-hole, wherein the cover is disposed on the insulation layer, and the vent-hole connects with the groove.

2. The electrode strip according to claim 1, wherein the electrode layer further includes a third electrode set disposed in response to the second reactive area.

3. The electrode strip according to claim 2, wherein the third electrode set is disposed adjacent to an end of the groove, and the third electrode set is configured to detect whether a sample flows over the surface of the groove.

4. The electrode strip according to claim 1, wherein the first protrusion and the second protrusion form a gap, and the gap is from about 0.1 mm to about 1.3 mm.

5. The electrode strip according to claim 4, wherein the vent-hole connects with the second reactive area, the vent-hole is configured to form a capillary attraction, and the capillary attraction drives a sample into the second reactive area from the first reactive area.

6. The electrode strip according to claim 4, wherein a first length includes a length of a short side of the first protrusion, a length of the gap, and a length of a short side of the second protrusion; a ratio of the first length to the first long side of the groove is from about 5% to about 30%, or a ratio of the first length to the second long side of the groove is from about 5% to about 30%.

7. The electrode strip according to claim 4, wherein a ratio of a is long side of the first protrusion to a short side of the groove is from about 60% to about 90%, or a ratio of a long side of the second protrusion to the short side of the groove is about 60% to about 90%.

8. The electrode strip according to claim 1, wherein a bottom of the first protrusion connects with the electrode layer, and a top portion of the first protrusion connects with the cover.

9. The electrode strip according to claim 8, wherein a bottom of the second protrusion connects with the electrode layer and a top portion of the second protrusion connects with the cover.

10. The electrode strip according to claim 1, wherein a surface area of the first reactive area is larger than a surface area of the second reactive area.

11. The electrode strip according to claim 1, wherein the first protrusion and the second protrusion are configured to alter the direction of a sample flowing into the groove.

12. The electrode strip according to claim 4, wherein the first protrusion and the second protrusion extend from opposing sides and form the gap between the first protrusion and the second protrusion.

13. The electrode strip according to claim 12, wherein a flowing length includes a length of a long side of the first protrusion, a length of a short side of the first protrusion, a length of the gap, a length of a short side of the second protrusion, and a length of a long side of the second protrusion, and the flowing length is from about 0.9 mm to is about 1.8 mm.

14. The electrode strip according to claim 13, wherein the flowing length is configured to postpone a sample reaching the second reactive area from the first reactive area so as to generate a delay time, and the delay time is about 0.4 sec to about 2.0 sec.

15. A measurement system with hematocrit correction, comprising:
   the electrode strip as in claim 1, wherein the first electrode set is configured to measure a hematocrit concentration; and
   a sensor configured to electrically connect with the electrode strip, and the sensor includes:
      a power source configured to transmit a direct current (DC) signal or an alternating current (AC) signal to the first electrode set;
      a detector configured to detect a first reactive value in response to the hematocrit concentration, and a second reactive value in response to the analyte concentration; and
      a microprocessor configured to calculate the hematocrit-corrected analyte concentration in response to the first reactive value and the second reactive value.

* * * * *